| United States Patent [19] | [11] 3,974,196 |
|---|---|
| Nakamura et al. | [45] Aug. 10, 1976 |

[54] METHOD FOR DISPROPORTIONATING ETHYLENICALLY UNSATURATED COMPOUNDS HAVING FUNCTIONAL ESTER GROUPS

[75] Inventors: Ryuichi Nakamura, Tokyo; Seiji Fukuhara, Yokkaichi; Shuichi Matsumoto, Yokohama; Koei Komatsu, Yokkaichi, all of Japan

[73] Assignee: Japan Synthetic Rubber Co., Ltd., Tokyo, Japan

[22] Filed: Nov. 26, 1974

[21] Appl. No.: 527,433

[30] Foreign Application Priority Data
Nov. 28, 1973  Japan.............................. 48-134171
July 29, 1974  Japan.............................. 49-85987

[52] U.S. Cl................... 260/410.9 R; 260/410.9 N; 260/593 R; 260/485 R; 260/465.9; 260/485 N; 260/561 N; 260/408; 260/613 R; 260/448.2 R; 260/465.8 R
[51] Int. Cl.²............................................ C11C 3/02
[58] Field of Search.............. 260/410.9 R, 410.9 N, 260/485 R, 485 N; 252/429 B

[56] References Cited
UNITED STATES PATENTS
3,725,305  3/1973  Wilkinson....................... 260/485 R
3,783,136  1/1974  Inakai............................ 260/485 R OTHER PUBLICATIONS
Haines, R. et al. Chemical Society Reviews vol. 4 No. 1 (1975).

Chemical Abstracts 79: 145945c.
Chemical Abstracts 77: 113786n.
Chemical Abstracts 78: 71279n.
Chemical Abstracts 77: 125933n.

*Primary Examiner*—Winston A. Douglas
*Assistant Examiner*—John F. Niebling
*Attorney, Agent, or Firm*—Oblon, Fisher, Spivak, McClelland & Maier

[57] ABSTRACT

A method for the conversion of an unsaturated compound having a functional group, characterized by contacting [1] at least one compound selected from the group consisting of carboxylic acid esters, nitriles, ketones, amides, and ethers and having a carbon-to-carbon double bond and no unsaturation at the position conjugate to said double bond, or a mixture of said compound [1] and [2] at least one compound selected from the group consisting of ethylenically unsaturated compounds having a carbon-to-carbon double bond and neither unsaturation at the position conjugate to said double bond nor a functional group, with a catalyst system consisting essentially of a combination of (A) at least one member selected from the group consisting of tungsten compounds, molybdenum compounds, and rhenium compounds, with (B) at least one organolaluminum compound having at least one carbon-to-aluminum bond.

12 Claims, No Drawings

METHOD FOR DISPROPORTIONATING ETHYLENICALLY UNSATURATED COMPOUNDS HAVING FUNCTIONAL ESTER GROUPS

This invention relates to a method for the conversion of unsaturated carboxylic acid esters, unsaturated nitriles, unsaturated ketones, unsaturated amides, and unsaturated ethers.

The hitherto known metathesis (the term "metathesis" used herein includes disproportionation) of unsaturated compounds is, for the most part, metathesis of alkenes carrying no functional group; there has scarcely been known metathesis of the unsaturated compounds carrying functional groups.

In German Pat. No. 2,063,150, one of the few reports, it is disclosed that crotonitrile is formed when acrylonitrile and propylene are allowed to react at a high temperature of about 500°C. by use of a solid catalyst $WO_3$—$SiO_2$, though the yield is only less than 5 percent and the selectivity is also low.

Further, it is stated in Kautschuk und GummiKunst., 24, 383 (1971) that by contacting a mixture of oleic acid, 2-hexane, and a large excess of polybutadiene with an excess of $WCl_6$—$EtAlCl_2$ at an elevated temperature of 150°C., there are formed 4-octene, 2-butene, an oxygen-containing carbon compound, and a compound having 13 carbon atoms. On re-inspection of the gaschromatogram shown in said report, however, it is found that the recognizable compounds are only those having 8 to 13 carbon atoms; also the yield is so low that such a procedure cannot be called an art for the conversion of unsaturated compounds.

The aforementioned facts show that it is a very difficult problem to effect metathesis of alkenes carrying functional groups, particularly when attention is paid to the fact that the catalysts employed in the above-mentioned attempts have a high activity as well as a high selectivity only when effecting metathesis of alkenes carrying no functional group, and also show that the effective catalyst for the metathesis of alkenes without functional groups is not necessarily an effective catalyst for the metathesis of alkenes carrying functional groups. This is supported by the fact that there have long been substantially no reports on the metathesis of alkenes carrying functional groups.

The only report concerning the relatively successful experimental results was published in 1972 by C. Boelhouwer et al. (Chem. Comm., p. 1221 (1972)). This report has won favorable appreciation as the first report in the world, which dealt with the metathesis of an alkene carrying a functional group. The report relates to the metathesis of natural higher fatty acid esters with a $(CH_3)_4Sn$—$WCl_6$ catalyst wherein an alkyltin compound stable to polar groups is employed to advantage. The reaction temperature is 70°C. which is rather high for the metathesis of a homogeneous system. The reaction is conducted by a special procedure, in which the reactants are introduced into the catalyst system maintained at an elevated temperature.

However, the catalyst and process features disclosed in the above-mentioned report are not satisfactory from the practical and industrial viewpoints because of a high toxicity resulting from the methyltin used and of the unfavorable reaction conditions.

The present inventors have long done extensive research on the metathesis of alkenes carrying functional groups, while always taking into consideration its important significance. After a great number of repeated attempts, it was found most surprisingly that when unsaturated carboxylic acid esters, unsaturated nitriles, unsaturated ketones, unsaturated ethers, or unsaturated N,N-dialkylamides which are described hereinafter are contacted with a catalyst system composed of a mixture of a tungsten, molybdenum, or rhenium compound and a methylaluminum compound in an appropriate proportion, the metathesis of the above functional group-containing unsaturated compounds proceeds even at room temperature in a high yield and a high selectivity.

The present inventors have further paid special attention to the above finding and patiently repeated the experiments in further detail and more extensively. As a result, it has been found that a catalyst system comprising a combination of a compound of tungsten, molybdenum, or rhenium and an organoaluminum compound other than the methylaluminum compound also exhibits activity, though in a somewhat lower degree, toward the metathesis of the above-mentioned compounds. It has further been found surprisingly that the above catalyst activity toward metathesis can be enhanced by using as a third component (C) those various compounds which are mentioned hereinafter.

An object of this invention is to provide a method for the conversion of an unsaturated compound carrying a functional group.

Another object of this invention is to provide a method for the conversion of an unsaturated carboxylic acid ester, an unsaturated nitrile, an unsaturated ketone, an unsaturated amide, and an unsaturated ether.

A further object of this invention is to provide a catalyst which is effective for the conversion of an unsaturated compound carrying a functional group.

Other objects and advantages of this invention will become apparent from the following description.

The characteristic features of this invention are the above-said novel process and effective catalyst used. More particularly, the features are that the reaction and/or the catalyst are quite novel, that the reaction and other operations can be carried out under mild conditions, that the desired products are obtained in high yield and/or high selectivity, that the toxicity of the catalyst is low, and that the catalyst is easily available. Consequently, it may be said that the technique provided by this invention is distinguished from the practical and commercial viewpoints.

The term "practicality" used herein means not only that according to the process of this invention, the product is obtained in a high yield and high selectivity and the toxicity of the catalyst is low, but also that the use value of the product itself is high, because by properly selecting the number of carbon atoms and the functional group of, for example, fatty acid esters, carboxylic acid esters of (higher) alcohols, ethers, or nitriles, it becomes possible to develop new synthetic methods and new uses for telechelic compounds, large ring musks and various perfumes including precursors thereof, bioactive substances of insects, base materials for cosmetics, natural higher carboxylic acids, or alcohols.

According to this invention, there is provided a method for the conversion of an unsaturated compound having a functional group, characterized by contacting [1] at least one compound having a carbon-to-carbon double bond and no unsaturation at the position conjugate to said double bond and selected from the group consisting of carboxylic acid esters, nitriles, ketones, amides and ethers, or a mixture of said [1] compound and [2] at least one compound selected from the group consisting of unsaturated compounds having a carbon-to-carbon double bond and neither unsaturation at the position conjugate to said double bond nor a functional group, with a catalyst system consisting essentially of a combination of (A) at least one member selected from the group consisting of tungsten compounds, molybdenum compounds, and rhenium compounds with (B) at least one organoaluminum compound having at least one carbon-to-aluminum bond.

In the compound [1] for use in this invention, i.e. those carboxylic acid esters, nitriles, ketones, amides, and ethers which have a carbon-to-carbon double bond and no unsaturation at the position conjugate to said double bond, the carbon atoms of said carbon-to-carbon double bond have attached directly thereto no other atoms than hydrogen and carbon. Examples of suitable compounds are those represented by the general formula:

$$R^1R^2C=CR^3X.$$

In the above formula, $R^1$ represents hydrogen, an alkyl group, a cycloalkyl group, an aralkyl group, an aryl group, or an alkenyl group; or $R^1$ may be hydrocarbon group other than said groups or a halohydrocarbon group, which does not interfere with reactivity; or $R^1$ may be X mentioned below. $R^1$ has preferably up to 15 carbon atoms. $R^2$ and $R^3$ represent independently hydrogen or $C_{1-3}$ alkyl groups, preferably hydrogen.

X represents a group which has a hydrocarbon group bearing a substituent Y mentioned below and which contains no conjugated double bond except that in benzene nucleus. Examples of X are

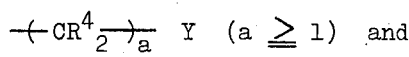  Y (a ≥ 1) and

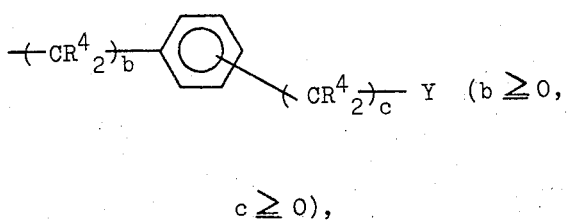

c ≥ 0), wherein $R^4$ represents chiefly hydrogen; at least one of $R^4$'s may be the same as Y or $R^1$ except X; and all of the $R^4$'s are not necessarily the same groups, though they are preferably hydrogen.

Y is —CN, —$COR^5$, —$OR^6$, —$CONR^7R^8$, —$NR^7COR^8$, —$OSiR^9R^{10}R^{11}$, —$SiR^9R^{10}OR^{11}$,

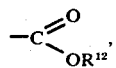

or —$OCOR^{13}$, wherein $R^5$ to $R^{13}$ represent alkyl groups, cycloalkyl groups, or aryl groups; or may be hydrocarbon groups other than said groups or halohydrocarbon groups, which do not interfer with reactivity. $R^5$ to $R^{13}$ have preferably up to 15 carbon atoms.

$R^5$ to $R^{13}$ containing an ester group are also suitable.

Examples of compounds (1) include ethyl vinylacetate, isobutyl vinylacetate, cyclohexyl vinylacetate, phenyl vinylacetate, ethyl 4-pentenoate, amyl 4-pentenoate, benzyl 4-pentenoate, propyl 3-decenoate, methyl 10-undecenoate, ethyl 10-undecenoate, methyl oleate, ethyl oleate, butyl oleate, methyl isooleate, ethyl 6-octadecenoate, butyl 6-octadecenoate, ethyl elaidate, butyl elaidate, methyl brassidate, methyl linolate, diethyl 2-allylmalonate, allyl acetate, oleyl acetate, 3-hexenyl acetate, oleyl oleate, 2-hexenyl 2-methylpropionate, 3-hexenyl valerate, 2-hexenyl acetate, allyl propionate, oleyl benzoate, 9-octadecenenitrile, 6-octadecenenitrile, 3-butenenitrile, 1,4-dicyano-2-butene, 4-pentenenitrile, octadecenedinitrile, 9,12-octadecadienenitrile, 9-decenenitrile, 10-undecenenitrile, 9-octadecenyl ethyl ether, 9-octadecenyl isopropyl ether, crotyl isopropyl ether, trimethylallyloxysilane, allylanisole, allyl phenyl ether, 8-heptadecenyl ethyl ketone, 5-heptadecenyl ethyl ketone, 5-hexen-2-one, 6-methyl-5-hepten-2-one, N,N-diethyloleamide, and N,N-diethylvinylacetamide. Beside the compounds represented by the aforesaid formula, there are also suitable cyclic ethers, cyclic ketones, and N-alkyllactams.

The unsaturated compounds [2] for use in this invention, which have a carbon-to-carbon double bond and neither unsaturation at the position conjugate to said double bond nor a functional group, are those in which the carbon atoms of said carbon-to-carbon double bond have attached directly thereto no atoms other than hydrogen and carbon, and are preferably aliphatic compounds represented preferably by the general formula, $R^{14}R^{15}C=CR^{16}R^{17}$, wherein $R^{14}$ and $R^{16}$ are hydrogen or $C_{1-3}$ alkyl groups, hydrogen being preferred and $R^{15}$ and $R^{17}$ represent hydrogen, alkyl groups, cycloalkyl groups, aralkyl groups, aryl groups, or other hydrocarbon groups such as alkenyl groups or halohydrocarbon groups which do not interfere with reactivity. $R^{15}$ and $R^{17}$ have preferably upto 15 carbon atoms.

Examples of compounds [2] are ethylene, propylene, 1-butene, 2-butene, 1-pentene, 1-hexene, 3-hexene, 3-heptene, 1-octene, 2-octene, 4-octene, 1-decene, 5-decene, 1-pentadecene, allylbenzene, p-chlorostyrene, 1,7-octadiene, 1,9-decadiene, oleyl chloride, 4-methyl-1-pentene, etc. 1,4-Polybutadiene and 1,2-polybutadiene may also be used.

Besides the above-said aliphatic compounds, there may also be used cyclic compounds represented by the general formula,

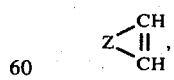

wherein —Z— represents $+CR^{18}_2\overline{)_d}$ ($d \geq 1$, excluding 4) or $+CR^{18}_2\overline{)_e}CR^{19}=CR^{20}+CR^{21}_2\overline{)_f}$ ($e \geq 1$ and $f \geq 1$, provided $e+f=3$) where $R^{18}$, $R^{19}$, $R^{20}$, and $R^{21}$ represent chiefly hydrogen; at least one of these R's may be selected from alkyl groups, cycloalkyl groups, aralkyl groups, aryl groups, those hydrocarbon groups other than the above-listed groups, such as alkenyl groups which do not interfere with reactivity, and those halohydrocarbon groups which do not interfere with reactivity (the above groups have preferably up to 15 carbon atoms). Two or more of the $R^{18}$'s and $R^{21}$'s may be different from one another.

Examples of the said cyclic compounds are cyclooctene, cycloheptene, cyclododecene, cyclododecatriene, cyclopentene, cyclobutene, and 1,5-cyclooctadiene, provided cyclohexene is excluded.

Beside the cyclic compounds represented by the above-mentioned general formula, there may be used bicycloalkenes such as norbornene and dicyclopentadiene and the like.

When the cyclic compound is used, the compound [1] must be present in excess so sufficient that a polymer may not be formed.

The tungsten, molybdenum, and rhenium compounds, which are used as the catalyst component (A) in this invention, include halides, oxyhalides, carbonyl complexes, alkoxides, alkenoxides, phenoxides, oxyalkoxides, alkoxy-halides, alkenoxy-halides, phenoxy-halides, nitrile complexes, and hydride complexes of tungsten, molybdenum, and rhenium. These compounds are used alone or in admixture of two or more. Mixtures of two or more compounds which form the above-mentioned compounds by reaction may also be used. Of the above-mentioned compounds, tungsten and molybdenum compounds are preferred and halides and alkoxy-halides of tungsten and molybdenum are particularly preferred.

Examples of the compounds are $WCl_6$, $WBr_6$, $WF_6$, $WI_6$, $MoCl_5$, $MoBr_5$, $MoCl_4$, $MoCl_3$, $ReCl_5$, $WOCl_4$, $MoOCl_3$, $W(CO)_6$, $Mo(CO)_6$, $Re_2(CO)_{10}$, $W(OC_6H_5)_6$, $WO(OCH_3)_4$, $WO(OCH_2.C_6H_5)_4$, $Mo(OC_2H_5)_2Cl_3$, $Mo(OC_2H_3)_2Cl_3$, $Mo(OC_6H_5)_2Cl_3$, $W(OC_6H_5)_4Cl_2$ and $Mo(CH_3CN)_3(CO)_2$. $WCl_6$, $MoCl_5$ and $Mo(OC_2H_5)_2Cl_3$ are particularly preferred.

As the organoaluminum compound which is the catalyst component (B) in this invention, there is used at least one compound having at least one carbon-to-aluminum bond, and usually, there may suitably be used compounds represented by the general formula:

where R represents an alkyl group, a cycloalkyl group, an aralkyl group, or an aryl group, $X^1$ represents a halogen, hydrogen, —OR, or —CN, and p is 1 to 3. Of these compounds, organoaluminum compounds in which R is a methyl group are particularly preferred for use.

Examples of the compounds represented by the above general formula include $(CH_3)_3Al$, $(CH_3)_2AlCl$, $(CH_3)_{1.5}AlCl_{1.5}$, $(CH_3)_2AlBr$, $(CH_3)_{1.5}AlBr_{1.5}$, $CH_3AlCl_2$, $(CH_3)_2AlOC_2H_5$, $(C_2H_5)_3Al$, $(C_2H_5)_2AlCl$, $(C_2H_5)_{1.5}AlCl_{1.5}$, $(C_2H_5)AlCl_2$, $(C_2H_5)_2AlF$, $(C_2H_5)_2AlI$, $(C_2H_5)_2AlH$, $(C_2H_5)_2AlOC_2H_5$, $(n-C_3H_7)_3Al$, $(iso-C_4H_9)_3Al$, $(iso-C_4H_9)_2AlCl$, $(n-C_6H_{13})_3Al$, $(n-C_8H_{17})_3Al$, $(cyclo-C_6H_{11})_3Al$, $(C_6H_5)_3Al$. Examples of compounds other than those represented by the above-mentioned general formula are $(CH_3)Al(C_2H_5O)Cl$, $(CH_3)_3AlN(CH_3)_3$, and $(C_6H_5)_3Al.Et_2O$. $(CH_3)_{1.5}AlCl_{1.5}$ is particularly preferred.

The ratio between the component (A) and the component (B) may vary depending upon the combination of the catalyst system, though (A)/(B) is usually in the range from 1/1 to 1/15 in terms of atomic ratio Me/Al (Me = W, Mo, or Re). The preferable ratio (A)/(B) is ½ to 1/6 when methylaluminum is used and 1/2.5 to 1/6 when other organoaluminum compounds are used.

The reactivity may be further enhanced when the reaction is conducted in the presence of a proper amount of a third component in addition to the components (A) and (B). The compounds for use as the third component are those having no conjugated double bond and include compounds having carbonyl group such as ketones, amides, aldehydes, esters, and quinones; compounds having phenolic hydroxyl group such as phenol and naphthol, or derivatives thereof; carboxylic acids and derivatives thereof; halohydrocarbons such as alkyl halides and vinyl halides; nitrophenols, alcohols, amines, water, acetals, ethers; and compounds of titanium, zirconium, potassium, boron, magnesium, aluminum, and vanadium having alkoxy group. The treatment with a gas such as carbon dioxide or oxygen is frequently effective to enhance the reactivity.

Examples of the above-said third component are n-butyl chloride, n-butyl bromide, dichloroethane, tetrachloroethylene, benzyl chloride, ethylene chlorohydrin, benzoyl chloride, acetic acid, trichloroacetic acid, trifluoroacetic acid, lactic acid, tetrahydrofuran, styrene oxide, ethyl ether, anisole, isobutyl vinyl ether, acetone, naphthoquinone, ethanol, n-decyl alcohol, phenol, p-chlorophenol, $\alpha$-nitroso-$\beta$-naphthol, dinitrophenol, nitrobenzene, triethylamine, ethanolamine, morpholine, acetamide, azobenzene, titanium tetrabutoxide, potassium butoxide, tributoxyboron, aluminum isopropoxide, magnesium ethoxide, benzaldehyde, acetal, water, oxygen, carbon dioxide, carbon disulfide, etc. Depending upon the ratio of the components (A) and (B) and the type of alkenes used as reactant, the effect of the third component on reactivity varies and also the amount of the third component necessary for the optimum reactivity often varies. Among the compounds for use as the third component, those having an aromatic ring bearing an electron attracting substituent, such as dinitrobenzene and p-chlorophenol, often give desirable results.

It is also possible to carry out the reaction by use of the catalyst system supported on a carrier usually employed in conventional solid catalysts or on an organic polymer such as a polymer containing carbonyl and/or hydroxyl group, e.g. polyvinyl acetate or its (partial) saponification product.

Depending upon the type of reaction, it is not always necessary to use as the catalyst components (A) and (B) the afore-listed compounds themselves; for example, methylaluminum compound may be formed in situ starting from a combination of aluminum chloride with methyllithium.

In this invention, although the reaction can be carried out either in the presence or in the absence of a solvent which does not interfere with the catalyst activity, it is preferable, if necessary, to use a suitable solvent. The solvent for use in this invention can be selected from a very wide range, and beside hydrocarbons and halohydrocarbons, even those ethers, esters, and nitriles which are inert to the catalyst may be used. That the reaction can be carried out in such polar solvents which could not be used heretofore is one of the important features of this invention.

Examples of suitable solvents include n-heptane, isooctane, hexadecane, benzene, toluene, decalin, cyclohexane, dichloroethane, hexamethylene dibromide, chlorobenzene, dichlorobenzene, diphenyl ether, diethyl ether, tetrahydrofuran, ethyl acetate, methyl stearate, and acetonitrile.

The temperature suitable for carrying out the present process is in the range from −30° to +300°C., preferably from −10° to +200°C. The reaction is conducted usually at atmospheric pressure, though it can be conducted at subatmospheric or superatmospheric pressure.

The invention is illustrated below in further detail with reference to Examples, but the invention is not limited thereto. In the Examples, unless otherwise indicated, the yield % was calculated based on the area of peak in gaschromatogram. The (total) metathesis yield was defined in a reaction AB + CD → BC + AD as $$\frac{\text{Area of peak in gaschromatogram for (BC + AD)}}{\text{Area of peak in gaschromatogram for (AB + CD) before reaction}} \times 100$$

provided that the yield of metathesis, if any, after isomerization is included. In most of the cases, an internal standard was employed in carrying out the gaschromatography to increase the accuracy of analysis. The yield of individual metathesis product was similarly calculated unless otherwise indicated.

EXAMPLE 1

To a thoroughly dried ampoule was added 5 ml of chlorobenzene, followed by 0.5 ml of a chlorobenzene solution of $(CH_3)_{1.5}AlCl_{1.5}$ (0.4 mole/liter), then 2 ml of a chlorobenzene solution of $WCl_6$ (0.05 mole/liter). Thirty seconds after the addition of the $WCl_6$ solution, 1 ml of methyl oleate was added to the ampoule and the ampoule was cooled to 0°C., then sealed off.

After 17 hours of reaction at 28°C., conversion of the methyl oleate was about 50% and selectivities for the main reaction products, 9-octadecene [I] and 8-hexadecene-1,16-dicarboxylic acid methyl ester (9-octadecenedioic acid dimethyl ester) [II], were 45% and 42%, respectively (stoichiometric selectivity was each 50%). It was surmised from the gaschromatogram that the by-products were the corresponding metathesis products after the double bond isomerization had occurred.

EXAMPLE 2

In the same manner as in Example 1, reaction was conducted by using 2 ml of a chlorobenzene solution of $MoCl_5$ (0.05 mole/liter) in place of the chlorobenzene solution of $WCl_6$ and at 26°C. for 20 hours. As the results, conversion of the methyl oleate was about 30% and selectivities for [I] and [II] were 42% and 40%, respectively.

EXAMPLE 3

Reaction was carried out in the same manner as in Example 1, except that 1 ml of methyl 10-undecenoate was used as the starting reactant in place of methyl oleate, the reaction temperature being 50°C. and the reaction time 4 hours. As the result, conversion of the methyl 10-undecenoate was 40% and the selectivity for 9-octadecene-1,18-dicarboxylic acid dimethyl ester (10-eicosenedioic acid dimethyl ester), which was the main reaction product, was about 40%.

EXAMPLE 4

Reaction was conducted in the same manner as in Example 1, except that 1 ml of oleyl acetate was used in place of the methyl oleate, the reaction temperature was 27°C., and the reaction time was 15 hours. Conversion of the oleyl acetate was about 40%, and selectivities for 9-octadecene and 9-octadecene-1,18-diyl diacetate, which were the main reaction products, were 30% and 26%, respectively. It was presumed from the gaschromatogram that most of the by-products were the products of metathesis which took place subsequent to double bond isomerization of the starting material and reaction products.

EXAMPLE 5

Reaction was conducted in the same manner as in Example 1, except that 1 ml of allyl acetate was used in place of the methyl oleate, the reaction temperature was 27°C., and the reaction time 15 hours. Conversion of the allyl acetate was about 7%, and the selectivity for 2-butene-1,4-diyl diacetate was about 30%.

EXAMPLE 6

Reaction was carried out in the same manner as in Example 1, except that 0.5 ml of ethyl 4-pentenoate was used in place of methyl oleate, the reaction temperature being 50°C., and the reaction time 17 hours. Conversion of the ethyl 4-pentenoate was 35% and the selectivity for diethyl 3-hexene-1,6-dicarboxylate (4-octenedioic acid diethyl ester) was about 25%.

EXAMPLE 7

Reaction was carried out in the same manner as in Example 1, except that 1 ml of butyl oleate was used in place of methyl oleate, the reaction temperature was 50°C., and the reaction time was 4 hours. Conversion of the butyl oleate was about 20% and selectivities for [I] and dibutyl 8-hexadecene-1,16-dicarboxylate (9-octadecenedioic acid dibutyl ester), which were the main reaction products, were about 22% and about 20%, respectively. It was presumed from the gaschromatogram that the by-products were mainly the metathesis products after isomerization had occurred.

EXAMPLE 8

Reaction was carried out in the same manner as in Example 1, except that 1 ml of methyl linolenate was used in place of methyl oleate, the reaction temperature was 50°C., and the reaction time was 17 hours. A metathesis product, as presumed from the gaschromatogram, was obtained in a yield of about 10%.

EXAMPLE 9

Reaction was conducted in the same manner as in Example 1, except that 1 ml of a chlorobenzene solution of $Mo(OC_2H_5)_2Cl_3$ (0.1 mole/liter) was used in place of the chlorobenzene solution of $WCl_6$, the reaction temperature was 50°C., and the reaction time was 17 hours. Conversion of the methyl oleate was about 20% and selectivities for [I] and [II], the main reaction products, were 20% and 15%, respectively. It was presumed from the chromatogram that the by-products were mainly the metathesis products after the double bond isomerization had occurred.

EXAMPLE 10

Reaction was carried out in the same manner as in Example 1, except that a mixture of 1 ml of methyl oleate and 1 ml of 2-octene was used in place of 1 ml of the methyl oleate, the reaction temperature was 70°C., and the reaction time was 17 hours. There were obtained methyl 9-undecenoate in a yield of about 5% and methyl 9-pentadecenoate in a yield of about 7% (estimated from the chromatogram). Besides, metathesis products were obtained independently from methyl oleate and 2-octene.

EXAMPLE 11

Reaction was carried out in the same manner as in Example 1, except that a mixture of 1 ml of methyl oleate and 1 ml of oleyl chloride in place of 1 ml of the methyl oleate, the reaction temperature was 26°C., and the reaction time 17 hours. There was obtained a product (about 5% yield) which was pressumed as methyl 18-chloro-9-octadecenoate. Besides, metathesis products were obtained independently from each of methyl oleate and oleyl chloride.

EXAMPLES 12–16

Into each of the glass ampoules (A), (B), (C), (D), and (E), which had been thoroughly dried and flushed with nitrogen to replace the air, was introduced 2 ml of methyl oleate followed by 2 ml of a toluene solution of $WCl_6$ (0.05 mole/liter). After 5 minutes of stirring, 0.2 ml, 0.4 ml, 0.6 ml, 1.2 ml, and 2.0 ml of a toluene solution of $(CH_3)_{1.5}AlCl_{1.5}$ (0.5 mole/liter) were added to the ampoules (A), (B), (C), (D), and (E), respectively, and reaction was conducted at 26°C. for 20 hours. From the ampoules (A), (B), (C), (D), and (E), there were obtained [I] in yields of about 1%, 7–8%, about 14%, 8–9%, and about 2%, respectively, and [II] in yields of 0.5–1.0%, about 4%, about 12%, 6–7%, and about 2%, respectively.

EXAMPLES 17–21

Into each of the glass ampoules (A), (B), (C), (D), and (E), which had been thoroughly dried and flushed with nitrogen to replace the air, was introduced 1 ml of methyl oleate followed by 2 ml of a chlorobenzene solution of $WCl_6$ (0.05 mole/liter). After 5 minutes of stirring, 0.2 ml, 0.4 ml, 0.6 ml, 0.8 ml, and 1.2 ml of a chlorobenzene solution of $(C_2H_5)_{1.5}AlCl_{1.5}$ (0.5 mole/liter) were added to the ampoules (A), (B), (C), (D), and (E), respectively, and reaction was conducted at 50°C. for 40 hours. From the ampoules (A), (B), (C), (D), and (E), there were obtained [I] in yields of about 0.1%, 4%, 15%, 8%, and 5%, respectively, and [II] in yields of about 0.05%, 3%, 19%, 8%, and 5%, respectively.

EXAMPLES 22–25

Into each of the glass ampoules (A), (B), (C), and (D), which had been thoroughly dried and flushed with nitrogen to replace the air, was introduced 15 ml of 1,2-dichloroethane used as solvent, followed by 1.5 ml of methyl oleate, then by 2 ml of a chlorobenzene solution of $WCl_6$ (0.05 mole/liter). After about 10 minutes of stirring, chlorobenzene solutions (0.2 mole/liter) of $(C_2H_5)_2AlCl$, $(CH_3)_{1.5}AlCl_{1.5}$, $(C_2H_5)_{1.5}AlCl_{1.5}$, and $(C_8H_{17})_3Al$; each solution being in an amount of 1.5 ml, were added to the ampoules (A), (B), (C), and (D), respectively, and reaction was conducted at 30°C. for 20 hours. From the ampoules (A), (B), (C), and (D), there was obtained [II] in yields of about 9%, about 15%, about 3%, and about 4%, respectively.

EXAMPLES 26–33

To each of the glass ampoules (A), (B), (C), (D), (E), (F), (G), and (H), which had been thoroughly dried and flushed with nitrogen to replace the air, was added 1 ml of methyl oleate. To the ampoules (A), (B), (C), (D), and (E) was added each 0.05 millimole of (A) tetrachloroethylene, (B) ethylene chlorohydrin, (C) trichloroacetic acid, (D) p-chlorophenol, and (E) dinitrophenol, respectively. To the ampoules (F) and (G) were added 1 ml of oxygen and 0.2 millimole of p-chlorophenol, respectively. To every ampoule was added 2 ml of a toluene solution of $WCl_6$ (0.05 mole/liter) and, after 5 minutes of stirring, 0.6 ml of a toluene solution of $(C_2H_5)_2AlCl$ (0.5 mole/liter). Reaction was carried out at 28°C. for 17 hours. From the ampoules (A)–(H), there was obtained [II] in yields of (A) 12%, (B) 11%, (C) 13%, (D) 16%, (E) 13%, (F) 7%, (G) 11%, and (H) 5%, respectively.

EXAMPLE 34

To a 30 ml glass ampoule, the air in which had been replaced by nitrogen, was added 5 ml of chlorobenzene used as solvent, followed by 2 ml of a chlorobenzene solution of $WCl_6$ (0.05 mole/liter), and then by 0.4 ml of a chlorobenzene solution of $(CH_3)_{1.5}AlCl_{1.5}$ (0.5 mole/liter). After about one minute of stirring, 1 ml of allyl phenyl ether $(C_6H_5OC_3H_5)$ was added to the ampoule and the ampoule was sealed off at 0°C. Reaction was conducted at 70°C. for 17 hours. The reaction product was identified as 2-butene-1,4-diyl diphenoxide [III] $(C_6H_5OCH_2CH=CHCH_2OC_6H_5)$. The yield of [III] was about 5%.

EXAMPLE 35

To a 30-ml glass ampoule, the air in which had been replaced by nitrogen, were added 5 ml of chlorobenzene and 4 ml of a chlorobenzene solution of $WCl_6$ (0.05 mole/liter), then 0.8 ml of a chlorobenzene solution of $(CH_3)_{1.5}AlCl_{1.5}$ (0.5 mole/liter). After about one minute of stirring, 1 ml of trimethylallyloxysilane $[(CH_3)_3SiOCH_2CH=CH_2]$ was added to the ampoule, and the ampoule was sealed off at 0°C. Reaction was carried out at 70°C. for 17 hours. 2-Butene-1,4-diyl bistrimethylsilyl ether [IV] $[(CH_3)_3SiOCH_2CH=CHCH_2OSi(CH_3)_3]$ was obtained as the reaction product in a yield of about 10%. The product was identified by comparing the retention time in gaschromatogram with that of a reference compound synthesized by a known method.

EXAMPLE 36

Reaction was carried out in the same manner as in Example 34, except that allylanisole $(CH_3OC_6H_4CH_2CH=CH_2)$ was used as the reactant in place of the allyl phenyl ether. Among the reaction products, 1,4-(bis-p-methoxyphenyl)butene-2 $(CH_3OC_6H_4CH_2CH=CHCH_2C_6H_4OCH_3)$ [V] and 1,3-(bis-p-methoxyphenyl)propene $(CH_3OC_6H_4CH_2CH=CHC_6H_4OCH_3)$ [VI] were identified by gaschromatography. The yield of [V] was about 10% and that of [VI] about 5%.

EXAMPLE 37

To a 50-ml two-necked round-bottom flask which had been flushed with nitrogen to replace the air, were added 10 ml of chlorobenzene, 2 ml of a chlorobenzene solution of $WCl_6$ (0.05 mole/liter), and 0.4 ml of a chlorobenzene solution of $(CH_3)_{1.5}AlCl_{1.5}$ (0.5 mole/liter). To the stirred flask was added 1 ml of 9-octadecenenitrile $[CH_3(CH_2)_7CH = CH(CH_2)_7CN]$ and the reaction was conducted at 132°C. for 3 hours. Among the reaction products, [I] and 9-octadecenedinitrile $[NC(CH_2)_7CH = CH(CH_2)_7CN]$ [VII] were identified by gaschromatography. The yield of [I] was about 3% and that of [VII] about 2%. The selectivities for [I] and [VII] were each 80% or higher.

EXAMPLE 38

Into a 30-ml glass ampoule which had been flushed with nitrogen to replace the air, were introduced 5 ml of chlorobenzene, 0.5 ml of 9-octadecenenitrile, and 2 ml of a chlorobenzene solution of $WCl_6$ (0.05 mole/liter). After about one minute of stirring, 0.6 ml of a toluene solution of $(CH_3)_{1.5}AlCl_{1.5}$ (0.5 mole/liter) was added to the ampoule which was then sealed off at 0°C. Reaction was conducted at 60°C. for 17 hours to obtain [I] in a yield of about 8% and [VII] in a yield of about 7%. Selectivities for [I] and [VII] were each about 60%. A considerable number of alkenes having different number of carbon atoms were obtained as by-products due to double bond isomerization and subsequent metathesis. The metathesis yield including these reaction products were about 25%.

EXAMPLE 39

Reaction was carried out in the same manner as in Example 38, except that the reaction temperature was 20°C. The yield of [I] was 1% and that of [VII] was 0.7%. The selectivity was 90% or higher.

EXAMPLE 40

Reaction was carried out in the same manner as in Example 38, except that 0.3 ml of a toluene solution of $(C_2H_5)_2AlCl$ (1 mole/liter) was used in place of $(CH_3)_{1.5}AlCl_{1.5}$ and the reaction time was 30 hours. The yield of [I] was 0.2–0.5% and that of [VII] 0.1–0.2%. The total metathesis yield was about 1%.

EXAMPLE 41

Reaction was carried out in the same manner as in Example 38, except that 4 ml of a chlorobenzene solution (0.05 mole/liter) of $W(CO)_6$, in place of $WCl_6$, and 1.2 ml of a toluene solution (0.5 mole/liter) of $(CH_3)_{1.5}AlCl_{1.5}$ were used. The yield of [I] was about 2% and that of [VII] was about 0.5%.

EXAMPLE 42

Reaction was conducted in the same manner as in Example 41, except that 2 ml of a chlorobenzene solution (0.1 mole/liter) of $Mo(OC_2H_5)_2Cl_3$, in place of $W(CO)_6$, was used. The yield of [I] was about 5% and that of [VII] about 3%. The total metathesis yield was about 15%.

EXAMPLE 43

Reaction was conducted in the same manner as in Example 41, except that 4 ml of a chlorobenzene solution (0.05 mole/liter) of $ReCl_5$, in place of $W(CO)_6$, was used. The yield of [I] was about 1% and that of [VII] about 0.5%.

EXAMPLE 44

Reaction was conducted in the same manner as in Example 38, except that 1.5 ml of a chlorobenzene solution (0.2 mole/liter) of $(C_2H_5)_3Al$, in place of $(CH_3)_{1.5}AlCl_{1.5}$, was used and the reaction time was 30 hours. The yield of [I] was about 0.5% and that of [VII] about 0.3%.

EXAMPLE 45

Reaction was conducted in the same manner as in Example 39, except that 0.5 ml of 8-heptadecenyl ethyl ketone $[CH_3(CH_2)_7CH = CH(CH_2)_7COC_2H_5]$ was used in place of the 9-octadecenenitrile. The reaction products were identified by gaschromatography as [I] and presumably 11-docosene-3,20-dione $[C_2H_5CO(CH_2)_7CH = CH(CH_2)_7COC_2H_5]$ [VIII]. The yield of [I] was about 3% and that of [VIII] about 2%.

EXAMPLE 46

Reaction was conducted in the same manner as in Example 38, except that 1 ml of 5-hexen-2-one was used in place of 9-octadecenenitrile. 5-Decene-2,9-dione $[CH_3CO(CH_2)_2CH = CH(CH_2)_2COCH_3]$ [IX] was obtained in a yield of 10 mole-%.

EXAMPLE 47

Reaction was conducted in the same manner as in Example 39, except that 1 ml of N,N-diethyloleamide $[CH_3(CH_2)_7CH = CH(CH_2)_7CON(C_2H_5)_2]$ [X] was used in place of 9-octadecenenitrile and the reaction time was 6 hours. The reaction products were identified by gaschromatography as [I] and bis-N,N-diethyl-9-octadecenediamide $[(C_2H_5)_2NCO(CH_2)_7CH = CH(CH_2)_7CON—(C_2H_5)_2]$ [XI]. The yield of [I] was about 3% and that of [XI] about 1%.

EXAMPLE 48

Reaction was conducted in the same manner as in Example 38, except that 0.5 ml of a chlorobenzene solution of $(iso-C_4H_9)_3Al$ (0.5 mole/liter) was used in place of $(CH_3)_{1.5}AlCl_{1.5}$. The yield of [I] was about 1% and that of [VII] was about 0.3%.

EXAMPLE 49

Reaction was conducted in the same manner as in Example 41, except that 1 ml of a chlorobenzene solution of $W(OC_6H_5)_6$ (0.2 mole/liter) was used in place of the chlorobenzene solution of $W(CO)_6$. The total metathesis yield was about 3%.

EXAMPLE 50

Reaction was conducted in the same manner as in Example 38, except that 5 ml of ethyl acetate was used in place of 5 ml of the chlorobenzene. The total metathesis yield was about 30%.

EXAMPLE 51

Reaction was conducted in the same manner as in Example 38, except that 5 ml of 1-hexene was added immediately after the addition of 0.5 ml of 9-octadecenenitrile. The yield of 9-decenenitrile $[CH_2 = CH(CH_2)_7CN]$ [XII] was 5%, that of 5-tetradecene $[CH_3(CH_2)_3CH = CH(CH_2)_7CH_3]$ [XIII] was 4%, that of 9-tetradecenenitrile $[CH_3(CH_2)_3CH =$ CH(CH₂)₇CN] [XIV] 4%, and that of 1-decene [CH₂= CH(CH₂)₇CH₃] [XV] 10%.

EXAMPLE 52

Into a dried 50-ml autoclave was introduced 1.6 ml of a chlorobenzene solution of (CH₃)₁.₅AlCl₁.₅ (0.5 mole/liter), followed by 4 ml of a chlorobenzene solution of WCl₆ (0.05 mole/liter), and then 10 ml of chlorobenzene and 2 ml of 9-octadecenenitrile. Ethylene was introduced under pressure into the autoclave until the pressure in the autoclave reached 50 kg/cm² (gauge). Reaction was carried out at room temperature for 17 hours while stirring continually by means of a magnetic stirrer. Formation of 9-decenenitrile [XII] was confirmed by gaschromatography. The yield was 5%.

EXAMPLE 53

Reaction was conducted in the same manner as in Example 34, except that 1 ml of allylanisole and 2 ml of 2-pentene in place of the reactant allyl phenyl ether.

Formation of crotylanisole (CH₃CH = CHCH₂—C₆H₅OCH₃) [XVI] and 2-pentenylanisole (CH₃CH₂CH = CHCH₂C₆H₅OCH₃) [XVII] was pressured by gaschromatography. Yields of [XVI] and [XVII] based on allylanisole were about 5% and about 6%, respectively.

EXAMPLE 54

Reaction was effected in the same manner as in Example 1, except that immediately after the addition of 1 ml of methyl oleate, 1 g of 1,2-polybutadiene (1,2-content: 87.4%, $\overline{M}n \div 30,000$) dissolved in 5 ml of chlorobenzene was added.

The resulting product was subjected to several reprecipitation operations with methanol and toluene to be purified, and then subjected to measurement of I.R. spectrum to find absorption due to the ester group at about 1,740 cm⁻¹. From this fact, it was confirmed that the ester group was introduced into the 1,2-polybutadiene.

What is claimed is:

1. A method for disproportionating an ethylenically unsaturated compound or a mixture of ethylenically unsaturated compounds, which comprises:

reacting at a temperature from −30°C to +300°C a compound (1) having the formula:

R¹R²C = CR³X wherein R¹ is hydrogen, C₁₋₁₅ alkyl, alkenyl or X; R² and R³ are independently hydrogen or C₁₋₃ alkyl, and X is a group having the formula:

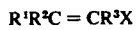

wherein Y is —C(=0)OR⁵ or —OCOR⁶ in which R⁵ and R⁶ represent C₁₋₁₅ alkyl or aryl; and R₄ represents principally hydrogen of C₁₋₁₅ alkyl and all of the R⁴ groups are not required to be the same, with the proviso that no sites of unsaturation exist at a position conjugate to the double bond, or a mixture of said compound and a compound selected from the group consisting of 1,4-polybutadiene; 1,2-polybutadiene; a compound having the formula,

wherein R⁷ and R⁹ are hydrogen or C₁₋₃ alkyl and R⁸ and R¹⁰ represent hydrogen, C₁₋₁₅ alkyl, aralkyl, aryl, or halohydrocarbon groups, with the proviso that no sites of unsaturation exist at a position conjugate to the double bond, or a cyclic compound having the formula,

wherein —Z— represents ─(CH₂)ᵦ─ or ─(CH₂)ᵧ─CH = CH ─(CH₂)ᵨ─ (b ≧ 1, c ≧ 1, d ≧ 1), with a catalyst consisting essentially of a combination of (A) at least one member selected from the group consisting of the halides, oxyhalides, carbonyl complexes, alkoxides, oxyalkoxides and alkoxyhalides of tungsten, molybdenum, or rhenium with (B) at least one compound having the formula, RₚAlX¹₃₋ₚ wherein R represents alkyl, X¹ represents halogen, hydrogen, or —OR and p is a number from 1 to 3, wherein the components (A) and (B) are used in such a ratio that the atomic ratio Me/Al, wherein Me is W, Mo or Re, falls within the range from 1/1 to 1/15.

2. The method according to claim 1, wherein the catalyst further contains as the third component a compound selected from the group consisting of n-butyl chloride, n-butyl bromide, dichloroethane, tetrachloroethylene, benzyl chloride, ethylene chlorohydrin, benzoyl chloride, acetic acid, trichloroacetic acid, trifluoroacetic acid, lactic acid, tetrahydrofuran, styrene oxide, ethyl ether, anisole, isobutyl vinyl ether, acetone, naphthoquinone, ethanol, n-decyl alcohol, phenol, p-chlorophenol, α-nitroso-β-naphthol, dinitrophenol, nitrobenzene, triethylamine, ethanolamine, morpholine, acetamide, azobenzene, benzaldehyde, acetal, water, oxygen, carbon dioxide, or carbon disulfide.

3. The method according to claim 1, wherein the compound is selected from the group consisting of ethyl vinylacetate, isobutyl vinylacetate, cyclohexyl vinylacetate, phenyl vinylacetate, ethyl 4-pentenoate, amyl 4-pentenoate, benzyl 4-pentenoate, propyl 3-decenoate, methyl 10-undecenoate, ethyl 10-undecenoate, methyl oleate, ethyl oleate, butyl oleate, methyl isooleate, ethyl 6-octadecenoate, butyl 6-octadecenoate, ethyl elaidate, butyl elaidate, methyl brassidate, methyl linolate, diethyl 2-allylmalonate, allyl acetate, oleyl acetate, 3-hexenyl acetate, oleyl oleate, 2-hexenyl 2-methylpropionate, 3-hexenyl valerate, 2-hexenyl acetate, allyl propionate, oleyl benzoate, 9-octadecenenitrile, 6-octadecenenitrile, 3-butenenitrile, 1,4-dicyano-2-butene, 4-pentenenitrile, octadecenedinitrile, 9,12-octadecadienenitrile, 9-decenenitrile, 10-undecenenitrile, 9-octadecenyl ethyl ether, 9-octadecenyl isopropyl ether, crotyl isopropyl ether, trimethylallyloxysilane, allylanisole, allyl phenyl ether, 8-heptadecenyl ethyl ketone, 5-heptadecenyl ethyl ketone, 5-hexen-2-one, 6-methyl-5-hepten-2-one, N,N-diethyloleamide, and N,N-diethylvinylacetamide.

4. The method according to claim 1, wherein the compound (2) is selected from the group consisting of ethylene, propylene, 1-butene, 2-butene, 1-pentene, 1-hexene, 3-hexene, 3-heptene, 1-octene, 2-octene, 4-octene, 1-decene, 5-decene, 1-pentadecene, allylbenzene, p-chlorostyrene, 1,7-octadiene, 1,9-decadiene, oleyl chloride, and 4-methyl-1-pentene.

5. The method according to claim 1, wherein the compound (2) is selected from the group consisting of cyclooctene, cycloheptene, cyclododecene, cyclododecatriene, cyclopentene, cyclobutene, 1,5-cyclooctadiene, nobornene and dicyclopentadiene.

6. The method according to claim 1, wherein the component (A) of the catalyst is selected from the group consisting of $WCl_6$, $MoCl_5$, $MoCl_3$, $ReCl_5$, $W(CO)_6$, $W(OC_6H_5)_6$, and $Mo(OC_2H_5)_2Cl_3$.

7. The method according to claim 1, wherein the component (A) of the catalyst is selected from the group consisting of $WCl_6$, $MoCl_5$ and $Mo(OC_2H_5)_2Cl_3$.

8. The method according to claim 1, wherein the component (B) of the catalyst is selected from the group consisting of $(CH_3)_{1.5}AlCl_{1.5}$, $(C_2H_5)_3Al$, $(C_2H_5)_2AlCl$, $(C_2H_5)_{1.5}AlCl_{1.5}$, $(iso-C_4H_9)_3Al$ and $(n-C_8H_{17})_3Al$.

9. The method according to claim 1, wherein the component (B) of the catalyst is $(CH_3)_{1.5}AlCl_{1.5}$.

10. The method according to claim 1, wherein the components (A) and (B) are used in such a ratio that the atomic ratio Me/Al falls within the range from ½ to 1/6.

11. The method according to claim 2, wherein the third component of the catalyst is a compound which has an aromatic ring bearing an electron-attracting substituent.

12. The method according to claim 1, wherein the reaction temperature is in the range from −10°C. to +200°C.

* * * * *